United States Patent [19]

Mennen

[11] 4,108,729
[45] Aug. 22, 1978

[54] PAPER BOOKLET FOR PRESUMPTIVE DIAGNOSIS OF NEISSERIA GONORRHOEAE IN THE MALE

[75] Inventor: Frederick C. Mennen, La Porte, Ind.

[73] Assignee: U.S. Packaging Corp., La Porte, Ind.

[21] Appl. No.: 797,467

[22] Filed: May 16, 1977

[51] Int. Cl.² ............................................ C12K 1/04
[52] U.S. Cl. ......................... 195/127; 195/103.5 M; 23/253 TP
[58] Field of Search ................... 23/253 TP; 195/127, 195/103.5 R, 103.5 M

[56] References Cited

U.S. PATENT DOCUMENTS

| | | | |
|---|---|---|---|
| 3,511,608 | 5/1970 | Anderson | 23/253 TP |
| 3,642,450 | 2/1972 | Ericksson | 23/253 TP |
| 3,718,543 | 2/1973 | Lagomarsino | 195/127 X |
| 3,785,930 | 1/1974 | Ellis | 23/253 TP X |
| 3,876,503 | 4/1975 | Mennen | 195/127 X |
| 3,954,563 | 5/1976 | Mennen | 195/127 |
| 3,954,564 | 5/1976 | Mennen | 195/127 |
| 3,996,006 | 12/1976 | Pagano | 23/253 TP |

Primary Examiner—Morris O. Wolk
Assistant Examiner—Arnold Turk

[57] ABSTRACT

A paper booklet for presumptive diagnosis of Neisseria Gonorrhoeae in the Male comprising staggered strips, a to d, back to front of (a) a bibulous paper specimen collector, (b) a bibulous paper reagent impregnated strip, (c) a bibulous paper target strip to which is applied a drop of physiological saline in the target circle, and (d) an impervious strip of polymer-coated paper which is used to squeeze the drop of saline from strip (c) through strip (b) to permit the specimen collected on strip (a) to interact with reagent in strip (b) and create color which presumptively diagnoses Neisseria Gonorrhoeae in the male.

3 Claims, 9 Drawing Figures

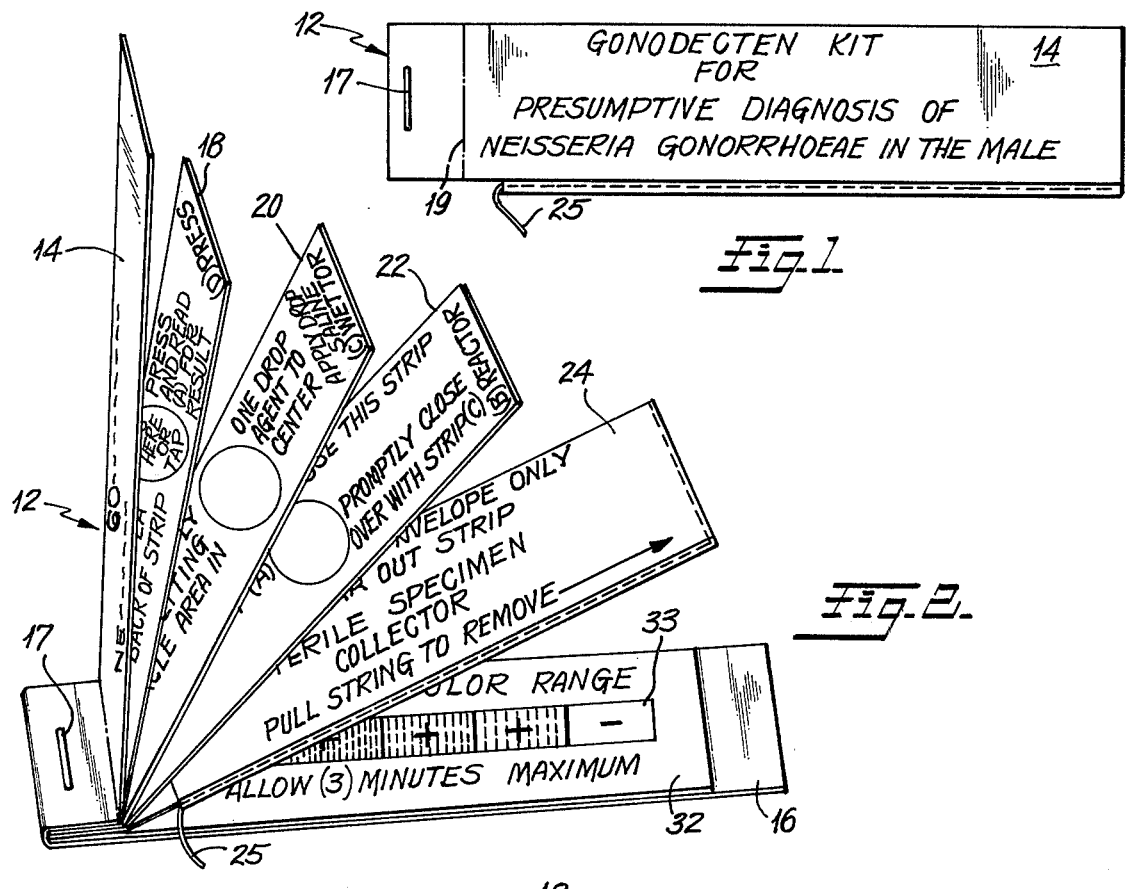
Fig. 1
Fig. 2
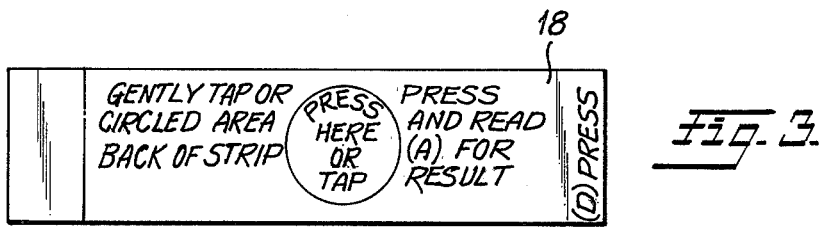
Fig. 3
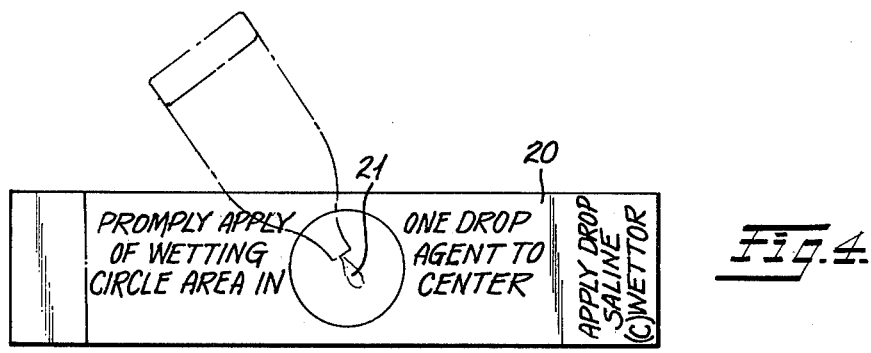
Fig. 4

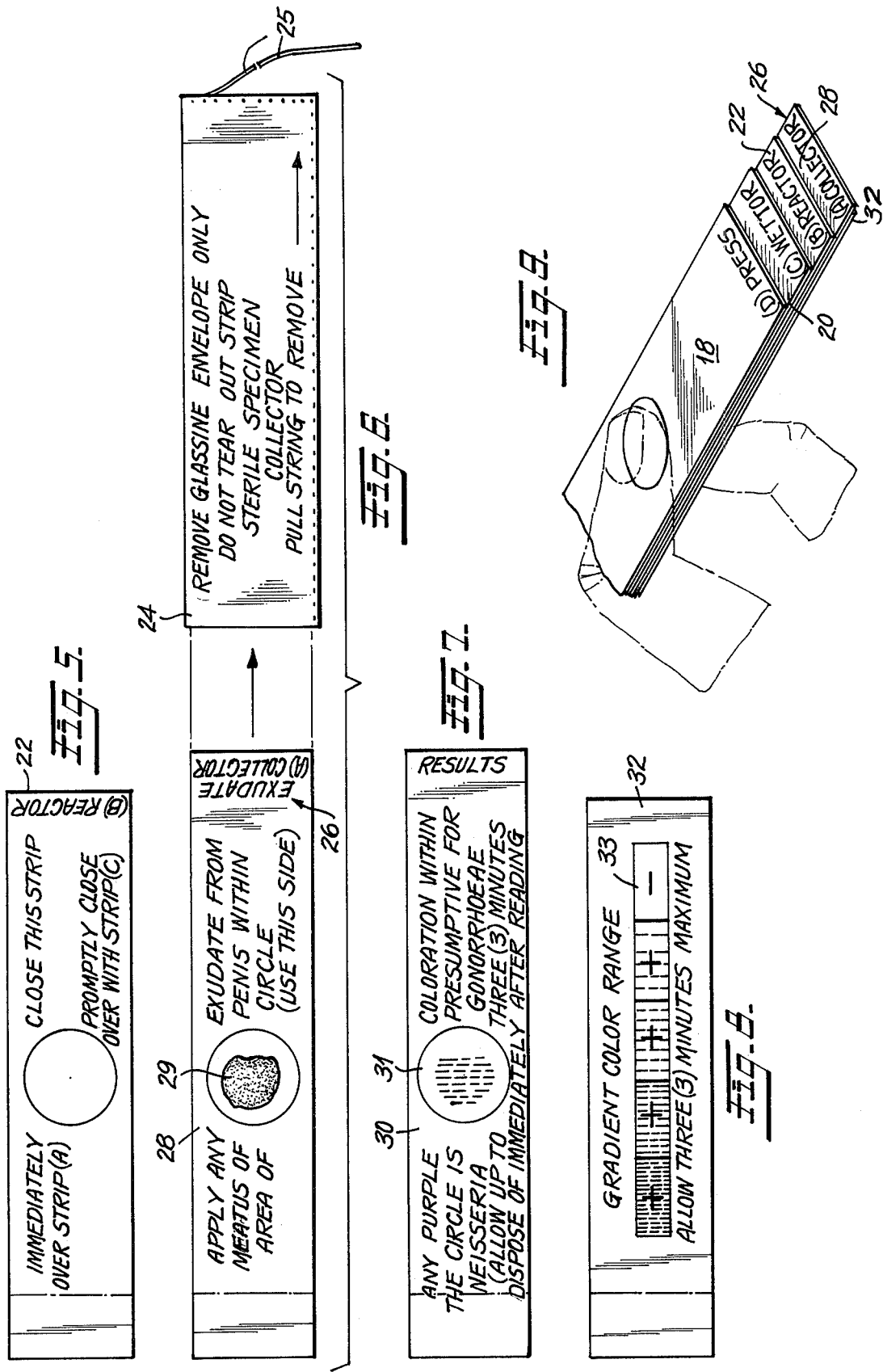

PAPER BOOKLET FOR PRESUMPTIVE DIAGNOSIS OF NEISSERIA GONORRHOEAE IN THE MALE

CROSS-REFERENCE TO RELATED APPLICATIONS

Frederick C. Mennen, Application filed Oct. 29, 1971, entitled Method and Instrument for the Detection of Neisseria Gonorrheae Without Culture, Now U.S. Pat. No. 3,876,503 granted Apr. 8, 1975.

Frederick C. Mennen, application filed Dec. 30, 1974, entitled Instrument for the Detection of Neisseria Gonorrhoeae, Ser. No. 537,593, allowed Oct. 20, 1976, Final Fee Paid Jan. 21, 1977, now U.S. Pat. No. 4,018,653 granted Apr. 19, 1977.

Frederick C. Mennen, application filed Mar. 28, 1975, entitled Apparatus Especially Useful for Detection of Neisseria Gonorrhoeae and the Like in Females, Ser. No. 563,300, granted May 4, 1976 now U.S. Pat. No. 3,954,563.

Frederick C. Mennen, Application filed Mar. 25, 1975, entitled Instrument for the Detection of Neisseria Gonorrhoeae and the Like, Ser. No. 561,707, granted May 4, 1976 now U.S. Pat. No. 3,954,564.

BACKGROUND OF THE INVENTION a. Field of The Invention

This invention is in the field of chemistry testing, specifically analytical and analytic control employing test papers and reagent carrier wherein the device is employed in a new manner to obtain an unexpected increase in sensitivity for the direct testing of Neisseria Gonorrhoeae.

b. Description of the Prior Art

The closest prior art on the system of testing for Neisseria Gonorrhoeae in the male is that shown in my recently issued application and granted patents which are listed as follows:
Frederick C. Mennen: U.S. Pat. No. 3,876,503
Frederick C. Mennen: U.S. Pat. No. 4,018,653
Frederick C. Mennen: U.S. Pat. No. 3,954,563
Frederick C. Mennen: U.S. Pat. No. 3,954,564

PATHOTEC PAPERS from Warner-Chilcott as described in Pedersen and Kelley, Public Health Report Vol. 81, No. 4,p. 318 (4/76), Kwalik JAMA Vol. 213 No. 4,p. 626 (7/70), British Journal of Venereal Disease, Vol. 43, p.73, and Acta Universitatis Carolinae Medica, Vol 27, No. 129, p. 47–50.

It is of interest to observe that test kits for determining the enzymes associated with microorganisms have long been provided for the laboratory investigator, the clinician, the medical research team and have found wide use in modern medical practice.

U.S. Pat. No. 3,644,177 discloses a test strip for determining penicillen content. The embodiment disclosed in FIGS. 4, 5 and 6 shows a test strip having a test pad 2 and blotting pad 4. The strip is notched at 5 to facilitate superposition of pads 2 and 4.

U.S. Pat. No. 3,888,741 discloses a test kit for identification of microorganisms comprising culturing means and an indicator for the microorganism being detected. (Neisseria Gonorrhoeae).

U.S. Pat. No. 3,642,450 discloses a test strip packaged-unit comprising a sealed envelope of plastic within which is subject to change in color by interaction with a sample to be tested. Parting lines 18 and 19 intermediate ends 16 and 17 (FIG. 5) permit envelope to be ripped off.

U.S. Pat. No. 3,699,003 discloses a diagnostic preparation for identification of streptococci comprising a carrier of bibulous material which contains a plurality of distinct areas.

U.S. Pat. No. 3,785,930 discloses a testing device including a folded-over transparent plastic sheet having a sheet of reagent impregnated fibrous material secured thereto. Color change is observed through the transparent sheet.

U.S. Pat. No. 3,917,453 discloses a testing device comprising an absorbent medium for the fluid to be tested and a reaction zone located between superposed sheets. Compressive force is applied to the absorbent medium providing a quantity of fluid to the reaction zone where reagents are located to react with the substance to provide colorimetric determination of the substance.

SUMMARY OF THE INVENTION

A paper booklet for presumptive diagnosis of Neisseria Gonorrhoeae in the male comprising staggered strips, a to d, back to front of (a) a bibulous paper specimen collector, (b) a bibulous paper reagent impregnated strip, (c) a bibulous paper target strip to which is applied a drop of physiological saline in the target circle, and (d) an impervious strip of polymer-coated paper which is used to squeeze the drop of saline from strip (c) through strip (b) to permit the specimen collected on strip (a) to interact with reagent in strip (b) and create color which presumptively diagnoses Neisseria Gonorrhoeae in the male.

The specimen of exudate which is collected from the meatus of the male penis on the bibulous paper specimen collector (a) receives the physiological saline from the target circle of the paper strip (c) which in turn picks up the chromogen reagent from the reagent stip (b) and color developes on the back side of the bibulous paper specimen collector (a). By opening the booklet the back of the bibulous paper specimen collector (a) is on one side of the open booklet and a Standard Gradient Color Range for comparison is provided on an additional leaf which lies below strip (a) on the other side of the booklet.

BRIEF DESCRIPTION OF THE DRAWINGS

FIG. 1 is a plan view of the testing packet of the present invention;

FIG. 2 is a perspective view of the packet of FIG. 1;

FIG. 3 is a plan view of the pressure leaf of the packet;

FIG. 4 is a plan view of the wettor leaf;

FIG. 5 is a plan view of the reactor leaf;

FIG. 6 is an exploded view of the collector leaf and its sterile covering envelope;

FIG. 7 is a bottom view of the collector leaf of FIG. 6;

FIG. 8 is a plan view of the color comparison leaf; and

FIG. 9 is a fragmentary respective illustrating the manner of pressing the packet leaves together in order to obtain a reading.

DESCRIPTION OF THE PREFERRED EMBODIMENT

In FIG. 1 there is shown a plan view of the testing packet of the invention which is provided in booklet form. The packet 12 of FIG. 1 is provided with a staple 17 at the left margin the fold or bend line 19 permitting the four essential bibulous paper strips to be opened in the manner shown in the perspective view of FIG. 2. The four basic strips used in sampling and testing are identified herein in assembled relation in FIGS. 2 and 9 and in separated relation in FIGS. 3, 4, 5, 6, 7 and 8. The relationship of each of the separate leaves, the pressure leaf of FIG. 3, the wettor of FIG. 4, the reactor leaf of FIG. 5 and the collector leaf of FIG. 6 is shown in the assembled view which bears the legend in FIG. 2. Thus, the pressure leaf of FIG. 3 is leaf 18 bearing the legend "GENTLY TAP OR PRESS CIRCLED AREA AND READ BACK OF STRIP (A) FOR RESULT". The "PRESS" portion is identified with the letter (D) and has the instruction "PRESS". To "PRESS" or "TAP" represents the active step to be carried out.

Similarly FIG. 4, which identifies the wettor reference (C) which legend is placed at the right margin, contains the instruction "APPLY DROP OF SALINE" to the identification of the function of this wettor solution. The instructions to the right of the target circle is "ONE DROP AGENT TO CENTER" of the target circle and a drop 21 of saline is shown applied to this leaf. The instructions immediately adjacent the fold line 19 is to "PROMPTLY APPLY ONE DROP OF WETTING AGENT TO CIRCLE AREA IN CENTER" which brings out the requirement for the critical time factor of less than 3 minutes in carrying out the test.

FIG. 3 is a plan view of the pressure leaf or strip of the packet: The pressure leaf is necessarily made of a the glassine or wax coated paper so that by tapping with the finger one would not risk infection by coming into contact with any toxic and reactive salts or any living bacteria that have reached the area through capillary action.

FIGS. 6 and 7 show both the upper and lower sides of exudate collector 26. The upper side 28 has a target circle 29 for receiving a sample to be tested and lower side 30 has a target circle 31 where developed color is viewed.

FIG. 8 shows the last leaf, leaf 32, of the kit or the bottom-outer cover. It is positioned and collated so that when the colorimetric result is observed on the back of the sterile exudate collector 26 it is on the opposite side of leaf 32 when the booklet is opened and there is thereby provided the "open book" effect so that easy reference and comparison can be made between its gradient range of leaf 32 which is the back of the open booklet and any color that might have occurred in the target circle on the reverse side of exudate collector 26 where the specimen of exudatewas collected. This color range comparison or guide leaf 32 shows the "GRADIENT COLOR RANGE" 33 and further bears the legend "ALLOW THREE (3) MINUTES MAXIMUM" to emphasize the criticality of the time factor.

CRITICAL CHROMOGEN IN STRIP (B) REACTOR (LEAF 22)

The critical chromogen is a reagent selected from the group consisting of: p-amino dimethylaniline oxalate, N, N-dimethyl-p-phenylenediamine dihydrochloride, N, N-dimethyl-p-phenylenediamine oxalate, N, N-dimethyl-p-phenylenediamine monohydrochloride and N, N, N'N' tetra-methyl-p-phenylenediamine dihydrochloride.

A preferred method for the manufacture of the chromogen strip 22 and the preparation of a wetting agent is illustrated as follows:

A 1% solution of N, N,N' N' tetra methyl-p-phenylene-diamine di- hydrochloride is prepared as follows: 1 gram of the reagent is added to 35 ml distilled water that has been brought to a boil and allowed to cool to room temperature. Solution is effected by rapid stirring. 64 ml of ethyl alcohol (Fisher A-407) is then added and stirred.

Strips of paper are dipped one at a time into the solution, placed on nylon screen in a horizontal position and allowed to air-dry. The dry strips are then cut into pieces.

A physiological saline solution is prepared by adding 0.85 grams of sodium chloride to 99 ml distilled water and the pH adjusted to 7.0. This solution is in the bottle shown in FIG. 4.

PREFERRED CHROMOGEN IN REACTOR STRIP B AND COMPARISON OF CHROMOGENS IN PATHOTEC PAPER

The preferred chromogen is the dihydrochloride salt of N, N, N' N' tetramethyl p-phenylene deamine based upon (1) its maximum sensitivity (serial dilution down to $10^{-3} - 10^{-4}$), ready activation by saline or water at neutral pH, and its toxic effect on the gonorrhoeae bacterium. The color developed, purple or purple blue, is early recognized and in the booklet in FIG. 9 leaf (b) is shown as strip 22 in FIGS. 2 and 5.

The sensitivity of the chromogen class and of the preferred chromogen is such that wetting as shown in FIG. 4 is essential in the form of neutral water or saline, the wetting of the target area of strip 22 by dropping water in the target circle of the wetter strip 20 assures that that collection of chromogen from strip 22 and then to strip 26 is carried out solely and exclusively by the 1-2 drops of saline passing through the collector strip 26 to cause capillary transfer of the exudate plus saline from the collector strip to the reactor strip 22 with the collector leaf (A) below the reactor leaf B as shown in FIG. 9. Simple digital manipulation at the target circle (see FIG. 9) accomplishes the capillary movement. The other leaf 32 is a representation of a standard in a Standard Gradient color range as illustrated in FIG. 2 and FIG. 8.

Other chromogens of the invention such as the oxalate have a pink color and are not toxic, so that they correlate with chromogens used in hospital solutions. Operator safety is obviously improved if the bacterium is killed by the preferred chromogen of the invention.

This chromogen toxicity is a problem to users of the booklet and a protective covering shown as 24 is provided with a pull string for removal as shown in FIG. 1; therefore an advantage of the invention to provide the covering in order to prevent contact, if the novel and unobvious precautions of the illustrated invention are scrupulously followed the booklet 12 is simple and safe. Thus, the packaging of the collector strip of the booklet in a sterile plastic wrap with pull string device 25 as shown in FIG. 2, the covering of the dangerous reactor leaf (B) with "PROMPTLY CLOSE" instructions as shown in FIGS. 2 and 9 and the digital manipulation of wetter leaf C as shown in FIG. 4 instructions which come with the booklet and facilitate proper use.

The outer top cover strip 14 of the booklet and the bottom outer cover strip 16 serve as the top and bottom covers respectively in the stapled relationship provided by staple 17.

In this connection, note that HEW Information Series 1945 revised 1970 identifies the aromatic amines as inducing bladder cancer. Obviously, a test paper which contains an aromatic amine must not touch the meatus of the penis nor the fingers of the operator.

Pathotec papers suffer from the foregoing defect; they contain reactive alpha naphthol and dimethylphenylene diamine which depend upon the exudate from the meatus for the volume solution of the test. Accordingly, such reagents work slowly (10 minutes) under acid pH to create an indophenol dye which gives excess false positives a very low reliability and are very prone to autooxidation.

PREFERRED BIBULOUS MATERIAL

The bibulous material must be relatively inert, iron-free of uniform thickness, and is between about 0.003 inches to 0.0011 inches in thickness, preferably about 0.006 to 0.009 inches. Any convenient width may be used, generally between about ⅝ inches and 1¼ inches. The porosity for the leafs A, B, and C, must be about that of good grade blotting paper to insure capillary action when wet by 1-2 drops neutral of coater or saline. The preferred material is available as filter paper in rolls and is of low ash content. Obviously, paper from only paper fibers are not the only materials since dacron cotton papers and the like may be used. The capillarity of the collector leaf (A) must be such that exudate or pus will not penetrate.

Having thus disclosed the invention, I claim:

1. A booklet for presumptive diagnosis of Neisseria Gonorrhoeae in the male consisting essentially of four staggered strips, (a) through (d), of bibulous iron-free absorptive material in overlying relation with (a) through (d) lying back to front in the booklet;

strip (a) being a bibulous collector strip having a target circle between its ends for collecting a sample of exudate from the meatus of a male penis in the target circle;

strip (b) overlying strip (a) being a reactor strip consisting of bibulous material impregnated with a chromogen reagent and being substantially color free;

strip (c) overlying strip (b) being a bibulous wettor strip having a wettor target circle overlying said target circle of said collector strip whereby one or two drops of physiological saline applied to the wettor target circle passes through strip (b) to carry chromogen reagent wet with said one or two drops into the target circle of said collector strip to create a color change on the back side of said strip (a) in the presence of Neisseria Gonnorrhoeae in the exudate applied to strip (a);

strip (d) overlying strip (c) consisting of polymer coated material serving to press the one or two drops of physiological saline through (c), (b) and (a);

a gradient color scale range strip located beneath strip (a) whereby subsequent to sampling and pressing, strip (a) can be lifted to achieve an open book effect to view the color change on the back of strip (a) against said gradient color scale range; and said chromogen reagent selected from the group consisting essentially of p-amino dimethylaniline oxalate, N, N-dimethyl-p-phenylenediamine dihydrochloride, N, N-dimethyl-p-phenylenediamine oxalate, N, N-dimethyl-p-phenylenediamine monohydrochloride and N. N. N' N' tetra-methyl-p-phenylenediamine dihydrochloride.

2. A booklet for presumptive diagnosis of Neisseria Gonorrhoeae in the male consisting essentially of four staggered strips, (a) through (d), of bibulous iron-free absorptive material in overlying relation with (a) through (d) lying back to front in the booklet;

strip (a) being a bibulous collector strip having a target circle between its ends for collecting a sample of exudate from the meatus of a male penis in the target circle;

a wrapping about strip (a) to maintain it sterile;

strip (b) overlying strip (a) being a reactor strip consisting of bibulous material impregnated with a chromogen reagent and being substantially color free;

strip (c) overlying strip (b) being a bibulous wettor strip having a wettor target circle overlying said target circle of said collector strip whereby one or two drops of physiological saline applied to the wettor target circle passes through strip (b) to carry chromogen reagent wet with said one or two drops into the target circle of said collector strip to create a color change on the back side of said strip (a) in the presence of Neisseria Gonorrhoeae in the exudate applied to strip (a);

strip (d) overlying strip (c) consisting of polymer coated material serving to press the one or two drops of physiological saline through (c), (b) and (a);

a gradient color scale range strip located beneath strip (a) whereby subsequent to sampling and pressing, strip (a) can be lifted to achieve an open book effect to view the color change on the back of strip (a) against said gradient color scale range; and said chromogen reagent selected from the group consisting essentially of p-amino dimethylaniline oxalate, N, N-dimethyl-p-phenylenediamine dihydrochloride, N, N-dimethyl-p-phenylene-diamine oxalate, N, N-dimethyl-p-phenylenediamine monohydrochloride and N, N, N' N' tetra-methyl-p-phenylenediamine dihydrochloride.

3. A booklet as claimed in claim 2 wherein said wrapper has a tear open string for removal of the wrapping.

* * * * *